(12) United States Patent
Rodriguez

(10) Patent No.: US 12,390,502 B2
(45) Date of Patent: Aug. 19, 2025

(54) METHOD FOR STIMULATING GROWTH OF BACTERIA IN THE GUT MICROBIOTA OF A MAMMAL

(71) Applicant: LESAFFRE ET COMPAGNIE, Paris (FR)

(72) Inventor: Bertrand Rodriguez, Lambersart (FR)

(73) Assignee: LESAFFRE ET COMPAGNIE, Paris (FR)

( * ) Notice: Subject to any disclaimer, the term of this patent is extended or adjusted under 35 U.S.C. 154(b) by 817 days.

(21) Appl. No.: 17/425,588

(22) PCT Filed: Jan. 22, 2020

(86) PCT No.: PCT/EP2020/051537
§ 371 (c)(1),
(2) Date: Jul. 23, 2021

(87) PCT Pub. No.: WO2020/152229
PCT Pub. Date: Jul. 30, 2020

(65) Prior Publication Data
US 2022/0096580 A1    Mar. 31, 2022

(30) Foreign Application Priority Data
Jan. 23, 2019   (EP) .................................... 19305090

(51) Int. Cl.
| | | |
|---|---|---|
| A61K 36/064 | (2006.01) | |
| A23C 9/127 | (2006.01) | |
| A23C 9/20 | (2006.01) | |
| A23L 31/15 | (2016.01) | |
| A61K 31/716 | (2006.01) | |
| A61P 1/12 | (2006.01) | |

(52) U.S. Cl.
CPC ............ *A61K 36/064* (2013.01); *A23C 9/127* (2013.01); *A23C 9/203* (2013.01); *A23L 31/15* (2016.08); *A61K 31/716* (2013.01); *A61P 1/12* (2018.01)

(58) Field of Classification Search
None
See application file for complete search history.

(56) References Cited

U.S. PATENT DOCUMENTS

| | | |
|---|---|---|
| 7,459,159 B2 | 12/2008 | Lesaffre |
| 2006/0292171 A1 | 12/2006 | Corthesy-Theulaz |
| 2010/0183767 A1 | 7/2010 | Noordam et al. |
| 2010/0196413 A1 | 8/2010 | Laville |
| 2010/0303778 A1 | 12/2010 | Simon |
| 2016/0287649 A1 | 10/2016 | Cani |
| 2017/0080015 A1 | 3/2017 | Heiman et al. |
| 2017/0321043 A1 | 11/2017 | Deremaux et al. |

FOREIGN PATENT DOCUMENTS

| | | |
|---|---|---|
| CN | 108041262 A | 5/2018 |
| EP | 2170359 B1 | 4/2010 |
| EP | 2870969 A1 | 5/2015 |
| EP | 3266863 A1 | 1/2018 |
| EP | 2227539 A2 | 9/2018 |
| FR | 3080521 A1 | 11/2019 |
| JP | 2007-501829 A | 2/2007 |
| JP | 2008-541700 A | 11/2008 |
| JP | 2018-503694 A | 2/2018 |
| JP | 2018-65812 A | 4/2018 |
| KR | 10-2006-0037432 A | 5/2006 |
| KR | 10-2010-0031634 A | 3/2010 |
| WO | WO 2005/021015 A1 | 3/2005 |
| WO | WO 2006/121803 A1 | 11/2006 |
| WO | WO 2009/013357 A1 | 1/2009 |
| WO | WO 2016/124927 A1 | 8/2016 |
| WO | WO 2019/170790 A1 | 9/2019 |
| WO | WO 2019/207111 A1 | 10/2019 |

OTHER PUBLICATIONS

Volman, Julia J; et al.; "Dietary modulation of immune function by β-glucans" Physiology Behavior, 94, 276-284, 2008 (Year: 2008).*
Notice of Reasons for Refusal dated Oct. 3, 2023 for Japanese Patent Application No. 2021-542410 in 9 pages.
Bircher, et al., Effect of cryopreservation and lyophilization on viability and growth of strict anaerobic human gut microbes, microbial biotechnology, pp. 721-733, 2018.
Bircher, et al., Cryopreservation of artificial gut microbiota produced with in vitro fermentation technology, microbial biotechnology, pp. 163-175, 2017.
De Vrese, et al., Probiotics and Prebiotics: Effectgs on Diarrhea, The Journal of Nutrition, American Society for Nutrition, pp. 803-811, 2007.
Doo, et al., Effect of dietary nucleosides and yeast extracts on composition and metabolic activity of infant gut microbiota in PolyFermS colonic fermentation models, FEMS Microbiology Ecology, 93, pp. 1-14, 2017.
European Search Report dated Jul. 23, 2019 in EP Application No. 19305090.3.
Gibson, et al., The International Scientific Association for Probiotics and Prebiotics (ISAPP) consensus statement on the definition and scope of prebiotics, Gastroenterology & Hepatology, vol. 14, pp. 491-502, 2017.
International Search Report mailed on Feb. 19, 2020 in International Application No. PCT/EP2020/051537.
Lynside Wall Basic, Technical Data Sheet, V07, pp. 1-2, 2016.

(Continued)

*Primary Examiner* — David W Berke-Schlessel
(74) *Attorney, Agent, or Firm* — Knobbe, Martens, Olson & Bear, LLP

(57) ABSTRACT

A method is for stimulating the growth of bacteria of the *Bacteroidetes* phylum in the gut microbiota of a mammal. The method includes administering a yeast product as a prebiotic agent to the mammal. The yeast product comprises the walls of yeast cells, such as those of the genera *Saccharomyces, Pichia, Candida, Kluyveromyces, Yarrowia* and/or *Wickehomomyces*, or a fraction thereof.

23 Claims, No Drawings

(56) References Cited

OTHER PUBLICATIONS

Lynside Wall Basic, Stimulates your immune system with unrefined yeast β-glucan ingredients, Lesaffre Human Care The Culture of Life, V2, 2013.

Pinheiro, et al. A yeast fermentate improves gastrointestinal discomfort and constipation by modulation of the gut microbiome: results from a randomized double-blin placebo-controlled pilot trial, BMC Complementary and Alternative Medicine; 17:441; 2017.

Possemiers, et al., A dried yeast fermentate selectively modulates both the luminal and mucosal gut microbiota and protects against inflammation, as studied in an integrated in vitro approach, J. Argic. Food Chem., 2013.

Ridaura, et al., Cultured gut microbiota from twins discordant for obesity modulate adiposity and metabolic phenotypes in mice, Science, 341 (6150), 2013.

Written Opinion mailed on Feb. 19, 2020 in International Application No. PCT/EP2020/051537.

Office Action dated Jul. 2, 2024, issued in Japanese Patent Application No. 2021-542410, in 11 pages.

Office Action issued in Korean Patent Application No. 10-2021-7026373 dated Oct. 23, 2024 in 23 pages.

European Office Action dated Jan. 3, 2025 for European Application No. 20 700 851.7, 2 pages.

Office Action dated Jan. 3, 2025 for European Application No. 20 700 851.7, 7 pages.

Office Action dated Jan. 28, 2025 in Japanese Patent Application No. 2021-542410, 9 pages.

Price, et al., Use of *Saccharomyces cerevisiae* fermentation product on growth performance and microbiota of weaned pigs during *Salmonella* infection, Journal of Animal Science, 88:3896-3908, 2010; doi: 10-2527/jas.2009-2728, 16 pages.

\* cited by examiner

METHOD FOR STIMULATING GROWTH OF BACTERIA IN THE GUT MICROBIOTA OF A MAMMAL

PRIORITY AND CROSS REFERENCE TO RELATED APPLICATIONS

This application is the U.S. National Stage Application under 35 U.S.C. § 371 of International Application No. PCT/EP2020/051537, filed Jan. 22, 2020, designating the U.S. and published in English as WO 2020/152229 A1 on Jul. 30, 2020, which claims the benefit of European Patent Application No. EP 19305090.3, filed Jan. 23, 2019. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention belongs to the field of human and/or animal nutrition and health. The present invention particularly relates to a yeast product for use as a prebiotic agent, and a composition comprising it. It also relates to the non-therapeutic use of a yeast product, and a composition comprising it, as a prebiotic agent. The yeast product, and the composition comprising it, stimulate the growth of bacteria of the *Bacteroidetes* phylum in the mammal gut microbiota, independently from the initial microbial composition of the donor and enterotype.

TECHNICAL BACKGROUND

Non-digestible oligosaccharides (NDOs) resist digestion and absorption in the human small intestine, so that they are completely or partially fermented in the large intestine. These carbohydrates help to maintain regularity of colonic functioning and may contribute to human health by reducing the risk of chronic diseases. A lot of NDOs are considered to be prebiotic agents.

The activity of a prebiotic agent on the mammal gut microbiota, particularly the human gut microbiota, can be evaluated on the basis of the growth of health-promoting bacteria such as Lactobacilli and Bifidobacteria, the decrease in intestinal pathogens and the increase or decrease in production of health-related bacterial metabolites. The latter include for instance straight short-chain fatty acids (SCFAs), such as acetate, propionate and butyrate, which are generally believed to be positive for colonic health, while ammonia and branched SCFAs are regarded as risk factors for colon carcinogenesis.

However, Lactobacilli and Bifidobacteria are two genera only constituting a minor group within the gut microbiome, particularly the human gut microbiota. They have received a lot of attention due to the initial definition of a prebiotic compound that mentioned that prebiotic compounds should selectively be fermented by specific bacterial groups including Bifidobacteria and Lactobacilli, thus resulting in potential health-promoting effects. As a result of this narrow definition, many of the initial studies focusing on prebiotic effects of novel fibres have been applying a targeted approach focusing on these two groups, thus neglecting the potential effect of prebiotics on a large amount of other gut microorganisms.

The gut microbiota comprises a huge diversity of microorganisms. For example, bacteria of the phyla Actinobacteria, *Bacteroidetes*, *Firmicutes* and Proteobacteria are present in the gut microbiota. The growth of some of these bacteria has proven beneficial, as they would promote a healthy fermentation and particularly increase the production of short chain fatty acids (SCFAs) such as acetate, propionate and butyrate.

There is therefore a need for providing new prebiotic agents suitable for stimulating mammal gut microbiota, and particularly for stimulating the growth of bacteria of the *Bacteroidetes* phylum.

SUMMARY OF THE INVENTION

It is a first object of the invention to provide a yeast product, or a composition comprising it, for use as a prebiotic agent for stimulating the growth of bacteria of the *Bacteroidetes* phylum, in the mammal gut microbiota; wherein the yeast product comprises the walls of yeast cells or a fraction thereof.

In some embodiments, the yeast product, or a composition comprising it, is selected from the group consisting of the genera *Saccharomyces*, *Pichia*, *Candida*, *Kluyveromyces*, *Yarrowia* and/or *Wickehomomyces*; preferably wherein the yeast is selected from the group consisting of the species *Saccharomyces cerevisiae*, *Pichia jadinii*, *Kluyveromyces marxianus*; more preferably wherein the yeast is *Saccharomyces cerevisiae*.

In some embodiments, the bacteria of the *Bacteroidetes* phylum are bacteria of the *Bacteroidia* class; preferably bacteria of the Bacteroidales order; more preferably bacteria of the Bacteroidaceae family; still more preferably bacteria of the *Bacteroides* genus; most preferably *Bacteroides ovatus* spp.

In some embodiments, the yeast product increases the ratio of the bacteria of the *Bacteroidetes* phylum versus the bacteria of the *Firmicutes* phylum in the mammal gut microbiota.

In some embodiments, the prebiotic agent is selected from the group consisting of deactivated whole yeasts, yeast cell walls, fractions of the yeast cell walls, or mixtures thereof.

In some embodiments, the yeast product is a fraction obtained using a disruption treatment of yeast; and preferably the yeast product is the insoluble fraction of yeast cells. The disruption treatment may be a biochemical treatment and/or a mechanical treatment. The mechanical disruption may be obtained using glass beads, pressurized homogenization, ultrasounds or microwaves. The biochemical treatment may be selected from the group consisting of autolysis, thermal plasmolysis, enzymatic hydrolysis, osmotic shock and/or repeated cycles of freezing-thawing.

In some embodiments, the yeast product is a soluble sub-fraction obtained by submitting whole yeast cells to a disruption treatment, preferably a thermal plasmolysis, separating a soluble fraction from an insoluble fraction, then treating the insoluble fraction with ribonucleases (E.C. 3.1.4.1) and glucanases (E.C.3.2.1), before separating a protein-rich insoluble sub-fraction from a soluble sub-fraction.

In some embodiments, the yeast product is a soluble sub-fraction obtained by submitting whole yeast cells to a disruption treatment, preferably a thermal plasmolysis, then treating the mixture obtained with ribonucleases (E.C. 3.1.4.1) and glucanases (E.C.3.2.1), before separating a protein-rich insoluble sub-fraction from a soluble sub-fraction.

In some embodiments, the yeast product has a β-glucan content (expressed as equivalent mass of glucose) from 15 to 50% by mass on a dry matter basis; and/or a mannan content (expressed as equivalent mass of mannose) from 10 to 40% by mass on a dry matter basis.

In some embodiments, the yeast product comprises, by mass on a dry matter basis, from 15 to 50% of a β-glucan content (expressed as equivalent mass of glucose), from 10 to 40% of a mannan content (expressed as equivalent mass of mannose), from 5 to 15% of additional proteins, from 5 to 15% of free nucleotides, from 2 to 8% of free amino acids and peptides of 1 kDaltons or less, 2% or less of oligosaccharides, from 6 to 11% of ashes and from 1 to 3% of fat components and a dry matter content of at least 90%.

In some embodiments, the yeast product does not stimulate the growth of bacteria of the *Bifidobacterium* genus; preferably bacteria of the Bifidobacteriaceae family; more preferably bacteria of the Bifidobacteriales order. In some embodiments, the yeast product does not stimulate the growth of bacteria of the *Lactobacillus* genus; preferably bacteria of the Lactobacillaceae family; more preferably bacteria of the Lactobacillales order.

In some embodiments, the yeast product, or the composition comprising it, is administered orally; preferably wherein the yeast product, or the composition comprising it, is administered orally at a daily dose from 500 mg to 15 g; preferably wherein the yeast product, or the composition comprising it, is administered orally at a daily dose from 500 mg to 5 g in up to 10 takings.

In some embodiments, the composition is formulated as a gum, a tablet, a capsule, a pill, a powder, granules or a suspension.

It is a second object of the invention to provide a yeast product, or a composition comprising it, as defined herein, for use for preventing or limiting gut pathologies such as diarrheas and irritable bowel syndrome, for stimulating immunity, for regulating glycemia and/or lipidemia, for treating or limiting metabolic disorders associated to obesity.

It is a third object of the invention to provide the non-therapeutic use of a yeast product, or a composition comprising it, as defined herein, as a prebiotic agent for stimulating the growth of bacteria of the *Bacteroidetes* phylum in the mammal gut microbiota; wherein the yeast product comprises the walls of yeast cells or a fraction thereof.

In some embodiments, the composition is a foodstuff or a food supplement; preferably a dairy product, a fruit-based product, a drink, a solid foodstuff or a food supplement.

The present invention makes it possible to address the need of the prior art. In particular, the invention provides a yeast product, or a composition comprising it, for stimulating the growth of bacteria of the *Bacteroidetes* phylum in the mammal gut microbiota. By "stimulating the growth" is meant increasing the population of bacteria of the *Bacteroidetes* phylum in the mammal gut microbiota and/or increasing its relative abundance versus other bacteria.

The yeast product comprises the walls of yeast cells or a fraction thereof. The yeast product, or the composition comprising it, is therefore suitable for use as a prebiotic agent. By "prebiotic agent" is meant a non-digestible or non-fully digestible food product that beneficially affects the host by selectively stimulating the growth and/or activity of one or a limited number of beneficial bacteria in the colon, thereby improving host health. Prebiotic agents differ from probiotic agents in that the prebiotic agent is not a living organism.

The inventors have shown that yeast, especially *Saccharomyces cerevisiae* or its derivatives, regulates the gut microbiota, particularly by stimulating the growth of bacteria of the *Bacteroidetes* phylum, such as bacteria of the *Bacteroides* genus. It has therefore been demonstrated that yeast products have a prebiotic potential on the gut microbiota, by positively and selectively impacting both its metabolism and its composition. This prebiotic potential is particularly beneficial for preventing or limiting gut pathologies such as diarrheas and irritable bowel syndrome, for stimulating immunity, for regulating glycemia and/or lipidemia, for treating or limiting metabolic disorders associated to obesity (e.g. glucose tolerance and fatty liver disease).

DETAILED DECRIPTION

The invention will now be described in more detail without limitation in the following description.

In a first aspect, the present invention relates to a yeast product, or a composition comprising it, for use as a prebiotic agent for stimulating the growth of bacteria of the *Bacteroidetes* phylum, in the mammal gut microbiota. In a second aspect, the present invention relates to the non-therapeutic use of a yeast product, or a composition comprising it, for use as a prebiotic agent for stimulating the growth of bacteria of *Bacteroidetes* phylum in the mammal gut microbiota.

In some embodiments, the mammal is a human.

In other embodiments, the mammal is an animal.

The therapeutic and non-therapeutic uses of the yeast product depend on the subject to whom or which it is administered.

If the subject is healthy, the yeast product may be administered for maintaining the well-being of the subject and for facilitating the functioning of the gastrointestinal tract. The yeast product may be used non-therapeutically e.g. as a food supplement, e.g. for preserving digestive comfort.

If the subject is affected or is at a risk of being affected by gastrointestinal disorders or any related condition, the yeast product may be administered for preventing, treating or limiting such disorders, and for restoring or preserving the normal functioning of the gastrointestinal tract. The yeast product may then be used therapeutically and be formulated as a pharmaceutical composition.

The yeast product comprises the walls of yeast cells or a fraction thereof. The inventors have shown that yeast cell walls or fractions thereof, particularly the sub-fractions detailed herein, are particularly advantageous.

The yeast may be selected from the group consisting of the genera *Saccharomyces, Pichia, Candida, Kluyveromyces, Yarrowia* and/or *Wickehomomyces*; preferably from the group consisting of the species *Saccharomyces cerevisiae, Pichia jadinii, Kluyveromyces marxianus*. More preferably, the yeast is *Saccharomyces cerevisiae* spp.

The yeast may in particular be baker's yeast and/or brewer's yeast.

Yeast comprises a cytoplasm surrounded by a cell membrane. The cytoplasm comprises intracellular compartments, including the nucleus, mitochondrion and Golgi. The cell membrane is surrounded by the cell wall. The space in-between the cell membrane and the cell wall forms the periplasma.

The yeast product may be selected from the group consisting of deactivated whole yeast, yeast cell walls, fractions of yeast cell walls, or mixtures thereof.

The yeast product comprising yeast cell walls may be obtained using conventional disruption treatments. Upon application of a disruption treatment, an insoluble fraction and a soluble fraction of yeast cells are obtained. The soluble fraction forms what is conventionally known as the "yeast extract", both terms being used interchangeably herein, and comprises mostly free amino acids including glutamic acid, peptides and minerals. The insoluble fraction comprises the yeast cell walls, polymers, polysaccharides, nucleotides and heat-coagulated proteins.

The disruption treatment may be a biochemical treatment and/or a mechanical treatment. The mechanical disruption may be obtained using glass beads, pressurized homogenization, ultrasounds or microwaves. The biochemical treatment may be selected from the group consisting of autolysis, thermal plasmolysis, enzymatic hydrolysis, osmotic shock and/or repeated cycles of freezing-thawing.

For example, the yeast product may be produced as the insoluble fraction of yeast cells, obtained after autolysis or enzymatic hydrolysis, essentially, by proteases, preferably leading to the solubilization of at least 50%, more preferably at least 60%, by weight of dry matter of the whole yeast cells, and preserving the structural polysaccharides of the yeast cell wall i.e. the β-glucans and mannans.

Lynside® Wall Basic is an example of commercially available yeast cell wall product suitable for implementing the claimed invention. Lynside® Wall Basic comprises from about 20% to about 29% β-1,3/1,6-glucans, from about 18% to about 25% mannans, and has a dry matter of at least 94%, by total weight of the product. The nutrient content of Lynside® Wall Basic is as follows: from about 10.0% to about 31.2% of protein, from about 10% to about 25% of lipids, from about 38% of total carbohydrate and from about 3% to about 9% of ash, by total weight of the product.

Methods for obtaining yeast cell walls or fractions thereof are known. For example, European application EP2170359, PCT application WO2005/021015 and PCT application WO2009/013357 disclose yeast products comprised of yeast cell walls, comprising specific total glucan and mannan dry matter content by weight, and a specific glycogen dry matter content by weight.

In some embodiments, the yeast product may be a soluble sub-fraction obtained by submitting whole yeast cells to a thermal plasmolysis, then treating the mixture obtained with ribonucleases (EC 3.1.4.1) and glucanases (EC 3.2.1), before separating the protein-rich insoluble sub-fraction from the soluble sub-fraction. The soluble sub-fraction obtained with this process comprises the yeast extract.

In alternative embodiments, the yeast product may be a soluble sub-fraction obtained by submitting whole yeast cells to a thermal plasmolysis, then separating the insoluble fraction from the soluble fraction i.e. the yeast extract, then treating the insoluble fraction obtained with ribonucleases and glucanases, before separating the protein-rich insoluble sub-fraction from the soluble sub-fraction. The soluble sub-fraction obtained with this process does not comprise the yeast extract.

Methods for obtaining such protein-rich insoluble sub-fractions and the soluble sub-fractions are disclosed in the French application FR 3080521 A1 (1853748) filed on 27 Apr. 2018 and its related PCT application WO 2019/207111 A1.

The protein-rich insoluble sub-fraction comprises less than 3% of nucleotides and at least 72% of proteins.

The final soluble sub-fraction e.g. the soluble sub-fraction not comprising the yeast extract comprises from 45 to 70% of carbohydrates by total weight of the soluble fraction. The carbohydrates comprise from 25 to 40% glucans and from 25 to 35% mannans by total weight of the carbohydrates. The soluble sub-fraction may also comprise nucleotides, when a treatment step with deaminases is carried out.

The thermal plasmolysis may be carried out at a temperature of at least 45° C., preferably between 70 and 95° C. during a time period according to those skilled in the art, preferably from 30 sec to 4 h, still preferably from 1 min to 3 h, more preferably from 40 min to 2 h. The step of treatment with ribonucleases and glucanases may be carried out at a temperature between 40 and 65° C., preferably 60° C., and during a time period from 8 to 24 h; preferably 18 h.

The step of treatment with ribonucleases and glucanases may also be carried out in the presence of deaminases.

The step of separating the protein-rich insoluble sub-fraction from the soluble sub-fraction can be carried out in ethanol, a solvent or supercritical $CO_2$ in order to eliminate lipids and increase the proportion of proteins.

The preparation of the yeast product may comprise a drying step, such as spray-drying, vacuum-drying, fluidized-bed drying, drum-drying and/or freeze-drying.

In some embodiments, the yeast product is preferably free of yeast cell membrane, yeast cytoplasm and cellular compartments, their derivatives, or mixtures thereof.

In some embodiments, the yeast product is not a yeast extract and does not comprise such a yeast extract. A yeast extract is the soluble fraction directly obtained by submitting whole yeast cells to a disruption treatment, such as a biochemical treatment and/or a mechanical treatment.

In some embodiments, the yeast product is not a live whole yeast, such as instant dry yeast or active dry yeast.

Preferably, the yeast product comprises glucans.

The yeast product, particularly the soluble sub-fractions described herein, may have a β-glucan content (expressed as equivalent mass of glucose) from 15 to 50%, preferably from 20 to 40%, more preferably from 20 to 30%, by mass on a dry matter basis.

Preferably, the glucan comprises β-1,3-glucans, β-1,6-glucans, or combinations thereof.

Preferably, the yeast product comprises mannans, either in a free form or in the form of mannoprotein complexes.

The yeast product may have a mannan content (expressed as equivalent mass of mannose) from 10 to 40%, preferably from 15 to 30%, more preferably from 18 to 25%, by mass on a dry matter basis.

The yeast product may comprise additional proteins, particularly in a content from 5 to 15%, preferably from 8 to 12%, by mass on a dry matter basis.

The yeast product may comprise free nucleotides, particularly in a content from 5 to 15%, preferably from 8 to 12%, by mass on a dry matter basis.

The yeast product may comprise free amino acids and peptides of 1 kDaltons or less, particularly in a content from 2 to 8%, preferably from 4 to 6%, by mass on a dry matter basis.

The yeast product may comprise oligosaccharides e.g. trehalose, particularly in a content of 2% or less, preferably about 1%, by mass on a dry matter basis.

The yeast product may comprise ashes, particularly in a content from 6 to 11%, preferably from 8% to 9%, by mass on a dry matter basis.

The yeast product may comprise fat components, particularly in a content from 1 to 3%, by mass on a dry matter basis.

The yeast product may have a dry matter content of at least 90%, preferably of at least 95%, more preferably of 98%.

In a specific embodiment, the yeast product, such as a soluble sub-fractions free of yeast extract, comprises, by mass on a dry matter basis, from 15 to 50% of a β-glucan content (expressed as equivalent mass of glucose), from 10 to 40% of a mannan content (expressed as equivalent mass of mannose), from 5 to 15% of additional proteins, from 5 to 15% of free nucleotides, from 2 to 8% of free amino acids and peptides of 1 kDaltons or less, 2% or less of oligosaccharides, from 6 to 11% of ashes and from 1 to 3% of fat components and a dry matter content of at least 90%.

The prebiotic potential of the yeast product according to the invention may e.g. be assessed using an in vitro short-term model simulating the fermentation in the human proximal colon.

A suitable model is the continuous Simulator of the Human Microbial Ecosystem, known as SHIME®, which has been used for many years and validated with in vivo parameters, and which consists of five sequential reactors modelling the stomach, the small intestine, and the three colon compartments (ascending, transverse and descending). Simplified versions have also been developed.

In vitro short-term simulation model allows establishing and testing representative microbial communities, which differ both in the composition and functionality in the different colon regions. The potential of a prebiotic agent on the metabolism of the gut microbiota may be assessed by monitoring and measuring different parameters relative to the overall microbial fermentation, the changes in microbial activity and the changes in the microbial community composition.

The overall microbial fermentation may be monitored by measuring the pH and gas production. The changes in microbial activity may be assessed by comparing the kinetics in the production of bacterial metabolites (including SCFAs and lactate). The changes in the microbial community composition may be assessed by quantifying specific bacterial sequences (16S rRNA genes) through amplification (targeted qPCR and 16S-based Illumina sequencing).

Monitoring the pH during a colonic incubation provides a good indication of the production of SCFA, lactate. In general, a pH drop is observed during the first 24 h of incubation due to the formation of SCFA and lactate. This pH drop is often followed by a pH increase during the next 24 h of incubation due to proteolytic fermentation.

Gas production is a good measure for overall microbial activity, and thus speed of fermentation.

SCFA production results from carbohydrate metabolism in the colon and is related with various health effects. The most abundantly produced SCFAs consist of acetate, propionate and butyrate. Whereas acetate can be used as an energy source for the host and as a potential substrate for lipid synthesis in the body, propionate reduces cholesterol and fatty acid synthesis in the liver (beneficial effect on metabolic homeostasis). Butyrate on the other hand, is a major energy source for colonocytes and induces differentiation in these cells (related to cancer prevention) as well as a modulator of the immune response in the gut mucosa (related to an increase in regulatory T cells' number). The total SCFA levels are reflective of the overall fermentation of test ingredients.

In some embodiments, the yeast product of the present invention stimulates the growth of bacteria of the *Bacteroidetes* phylum in the mammal gut microbiota independently from the initial microbial composition of the donor and enterotype. The yeast product may stimulate the growth of bacteria of the *Bacteroidia* class; preferably bacteria of the Bacteroidales order; more preferably bacteria of the Bacteroidaceae family; still more preferably bacteria of the *Bacteroides* genus; most preferably *Bacteroides ovatus* spp.

In some embodiments, the yeast product does not stimulate the growth of bacteria of the Bifidobacteriales order; preferably bacteria of the Bifidobacteriaceae family; more preferably bacteria of the *Bifidobacterium* genus. Likewise, the yeast product may not stimulate the growth of bacteria of the Lactobacillales order; preferably bacteria of the Lactobacillaceae family; more preferably bacteria of the *Lactobacillus* genus.

In some embodiments, the yeast product increases the ratio of the bacteria of the *Bacteroidetes* phylum versus the bacteria of the *Firmicutes* phylum. It has been reported that the *Bacteroidetes* versus *Firmicutes* ratio is higher in lean subjects as compared to obese ones. Furthermore, increase in this ratio has been associated in prevention of obesity related disorders (weight gain, glucose intolerance or fatty liver disorders).

The yeast product may be administered orally. The yeast product may be administered at a daily effective dose, for example at a daily dose from 500 mg to 15 g. The daily effective dose may be administered up to ten takings, for example one, two, three, four or more takings. The yeast product may be administered as such or in a composition, in a form more suitable for oral administration.

The composition may be a pharmaceutical composition. The pharmaceutical composition may comprise any suitable pharmaceutically acceptable carrier or excipient. The pharmaceutical composition may further comprise one or more pharmaceutical active agents.

The composition may also be a foodstuff and/or food supplement. The composition may be a dairy product, a fruit-based product, a drink, a solid foodstuff or any other suitable edible product. The composition may be a nutraceutical composition, a dietary supplement or any other suitable food supplement.

The composition may be a liquid, a paste or a solid composition.

The composition may comprise one or more additional components. The additional components may be vitamins (for example A, C, D, E, K, B1, B2, B3, B5, B6, B8, B9, B12 or mixtures thereof), minerals (for example calcium, phosphorus, sodium, magnesium, iron or mixtures thereof).

The composition is preferably free of yeast extract.

The composition is preferably free of a live whole yeast, such as instant dry yeast or active dry yeast.

The yeast product may be formulated as a tablet, a capsule, a pill, a powder, a gum, granules or a suspension. If formulated as a powder or granules, the prebiotic agent, or the composition comprising it, may be packaged in a sachet or any suitable alternative packaging.

EXAMPLES

The following examples illustrate the invention without limiting it.

Example 1—In Vitro Assessment of Prebiotic Potential of a Yeast Cell Wall Fraction Summary—The enrichment of microorganisms from six representative microbiomes was studied, from a representative set of donors selected according to the donor stratification in enterotype (Arumugam M, et al. (2011) Enterotypes of the human gut microbiome. *Nature* 474(7353):666-666; Costea P I, et al. (2018) Enterotypes in the landscape of gut microbial community composition. *Nat Microbiol* 3(1):8-16.), on minimal media supplemented with Lynside® Wall Basic. Diluted fecal slurries were selectively enriched on medium supplemented with Lynside® Wall Basic using strict anaerobic culture techniques. Cultivation was performed for 48 h in order to allow growth on the complex substrate. Metabolite production and changes in microbiome composition after 48 h of enrichment were analyzed and compared to non-selective enrichments and a non-supplemented minimal medium in order to identify functional groups predictive for response to the tested fiber substrate.

Prebiotic Agent—Lynside® Wall Basic

Preparation of the inoculum—Fresh fecal samples from six donors representative of the three described enterotypes (i.e. *Ruminococcus*, *Prevotella* and *Bacteroides*) were used as inoculum for substrate utilization experiments. Two aliquots of 200 g were collected for each fresh fecal sample, 978 µL of 50 mM EDTA solution was added to each aliquot for stabilization and the aliquots were stored at −20° C. for subsequent extraction and microbiota profiling. Two aliquots of 1 mL of the 1:10 diluted fecal slurry used for inoculation were collected and centrifuged at 16000 g for 5', the supernatant was removed, 978 µL of 50 mM EDTA solution were added to the pellet for protection and the pellet was stored at −20° C.

Substrate enrichment—Experiments starting from fecal sample dilutions of the six donors were performed in triplicates in M2-based minimal medium with and without Lynside® Wall Basic supplementation and in broth M2GSC medium (Miyazaki K, Martin J., Marinsek-Logar R, Flint H. (1997) Degradation and Utilization of Xylans by the Rumen Anaerobe *Prevotella bryantii* (formerly *P. ruminicola* subsp. *brevis*) B14. Anaerobe 3(6):373-381), resulting in 54 enrichments. Enrichments were performed for 48 h at 37° C. From each enrichment, 1 mL of culture was centrifuged at 16000 g for 5', the supernatant was removed, 978 µL of 50 mM EDTA solution was added to the pellet for stabilization and the pellet was stored at −20° C.

SCFA analysis—The SCFA analysis is an assessment of the microbial carbohydrate metabolism i.e. the relative metabolite concentration after 48 h of incubation of acetate, propionate and butyrate.

Metabolic profiles of the six fecal samples and supernatants with and without Lynside® Wall Basic supplementation were determined by high performance liquid chromatography (HPLC). HPLC analysis was performed with a Hitachi LaChrome device (Merck, Switzerland) using a SecurityGuart™ Carbo-H+ cartridge (4×32 mm) connected to a Resex™ ROA-Organic Acid H+(8%) column (300×7.8 mm). Analysis was carried out with an injection volume of 40 µL, at a temperature of 80° C. and with a flow rate of 0.6 mL/min. $H_2SO_4$ (10 mM) containing sodium azide (0.005%) was used as eluent. Metabolite concentrations were quantified by refractive index (RI) detection. The detection limits (mM) for the three analytes were as follows: 2.06 mM for acetate, 1.61 mM for propionate and 1.55 mM for butyrate. The quantification limits (mM) for the three analytes were as follows: 6.23 mM for acetate, 4.89 mM for propionate and 4.69 mM for butyrate.

Results of the SCFA analysis—The SCFA concentrations obtained are shown in table 1 below:

TABLE 1

| Spl | Tr | L | ΔA | ΔP | ΔB |
|---|---|---|---|---|---|
| D1 | #1 | w/ | 14.16 | 6.83 | 5.08 |
| D1 | #2 | w/ | 14.24 | 6.36 | 4.83 |
| D1 | #3 | w/ | 15.36 | 6.95 | 6.27 |
| D2 | #1 | w/ | 11.73 | 1.64 | 2.77 |
| D2 | #2 | w/ | 8.45 | 2.32 | 2.31 |
| D2 | #3 | w/ | 9.93 | 3.33 | 2.42 |
| D3 | #1 | w/ | 14.52 | 5.67 | 5.41 |
| D3 | #2 | w/ | 14.34 | 3.54 | 6.44 |
| D3 | #3 | w/ | 15.67 | 1.93 | 5.22 |
| D4 | #1 | w/ | 11.18 | 2.61 | 4.95 |
| D4 | #2 | w/ | 10.61 | 1.96 | 7.21 |
| D4 | #3 | w/ | 9.83 | 5.42 | 6.78 |
| D5 | #1 | w/ | 9.07 | 5.79 | 9.64 |
| D5 | #2 | w/ | 9.22 | 8.82 | 7.86 |
| D5 | #3 | w/ | 11.92 | 8.03 | 6.45 |
| D6 | #1 | w/ | 8.84 | 0.93 | 2.44 |
| D6 | #2 | w/ | 11.72 | 0.97 | 5.11 |
| D6 | #3 | w/ | 9.36 | 1.64 | 5.44 |
| D1 | #1 | w/o | 8.05 | 1.86 | 2.70 |
| D1 | #2 | w/o | 7.17 | 0.96 | 4.75 |
| D1 | #3 | w/o | 8.52 | 1.83 | 4.54 |
| D2 | #1 | w/o | 8.13 | 1.45 | 2.56 |
| D2 | #2 | w/o | 5.82 | 2.00 | 4.69 |
| D2 | #3 | w/o | 6.89 | 1.47 | 2.89 |
| D3 | #1 | w/o | 8.34 | 0.66 | 3.23 |
| D3 | #2 | w/o | 8.91 | 1.58 | 3.32 |
| D3 | #3 | w/o | 9.37 | 1.43 | 2.76 |
| D4 | #1 | w/o | 6.64 | 0.63 | 1.85 |
| D4 | #2 | w/o | 6.50 | 0.76 | 3.75 |
| D4 | #3 | w/o | 5.41 | 1.09 | 4.38 |
| D5 | #1 | w/o | 7.14 | 1.48 | 1.74 |
| D5 | #2 | w/o | 6.72 | 0.75 | 1.11 |
| D5 | #3 | w/o | 7.47 | 0.94 | 1.62 |
| D6 | #1 | w/o | 6.30 | 3.48 | 3.41 |
| D6 | #2 | w/o | 6.01 | 0.95 | 3.88 |
| D6 | #3 | w/o | 6.38 | 3.82 | 3.25 |

Note
"Spl" for donor sample (amongst 6);
"Tr" for the number of the test for each donor (made in triplicate);
"w/L" or "w/o L" for tests carried out with and without Lynside ® Wall Basic supplementation;
"ΔA" for the acetate concentration (mM);
"ΔP" for the propionate concentration (mM);
and "ΔB" for the butyrate concentration (mM).

DNA microbial extraction—Extraction of microbial DNA was performed for one frozen aliquot from fresh fecal samples of each donor, one pellet of the 1:10 dilution of the fecal matter, and for all pellets collected from the enrichment experiments. Microbial DNA was extracted using the FastDNA™ SPIN Kit for Soil (MP Biomedicals, USA) as indicated by the producers. Quality of DNA extracts was confirmed on a TAE-1.5% agarose gel, and the concentration of total DNA of the extracted samples was determined by dsDNA Qubit assay using a Tecan Spark M10 multimode plate reader.

16S rRNA gene amplicon sequencing—Microbial composition was determined by 16S rRNA gene amplicon sequencing of the V3V4 region. Sequencing was performed on the MiSeq (Illumina, USA) platform using the MiSeq v3 paired-end reagent kit obtaining ca. 7 Mio. good quality stitched reads (average 17 k reads per sample, and average 51 k per treatment) of about 450 bp length.

Bioinformatic processing—The raw reads were trimmed, merged and quality filtered. Operational taxonomic units (OTU) picking was performed using the denoising algorithm unoise3 (cf. Edgar R C (2016) UNOISE2: improved error-correction for Illumina 16S and ITS amplicon sequencing. bioRxiv:81257). A first taxonomic classification of the obtained OTUs was performed using the Human intestinal tract database (HITdb—Ritari J, Salojärvi J, Lahti L, de Vos W M (2015) Improved taxonomic assignment of human intestinal 16S rRNA sequences by a dedicated reference database. *BMC Genomics* 16(1):1056) with a final manual refinement using a phylogenetic tree with the HITdb and the obtained 881 OTUs (with no singletons).

Results—Next generation sequencing of the 16S rRNA gene amplicon of the V3V4 variable regions was performed on the total bacterial DNA of the fecal samples.

The key objective was to identify the phylogenetic taxa selectively promoted by the studied substrate Lynside® Wall Basic. Therefore, all sequenced samples were categorized into three experimental groups: (1) Donor samples, including fecal samples from the six donors and a 1:10 dilution, respectively; (2) Lynside samples, composed of all samples from enrichments in minimal medium supplemented with the test substrate Lynside® Wall Basic; and (3) Negative control enrichments in minimal medium without substrate supplementation.

In a cross-comparison including all samples, a linear discriminant analysis (LDA—Segata N, et al. (2011) Metagenomic biomarker discovery and explanation. Genome Biol 12(6):R60) was performed to identify the phylogenetic taxa significantly (LDA≥2) enriched in either one of the three experimental groups as compared to all other groups. LDA scores revealed that enrichments in medium supplemented with the studied substrate Lynside® Wall Basic showed a significant increase of phylogenetic taxa belonging to the phylum *Bacteroidetes* by up to four orders of magnitude. The promotion of representatives within the phylum of *Bacteroidetes* upon Lynside® Wall Basic supplementation was observed in all donors, independently of their enterotype or initial *Bacteroidetes* abundance.

The LDA scores obtained are shown in table 2 below:

TABLE 2

| Sample | Phylogenetic taxa | LDA score | p-value |
|---|---|---|---|
| With Lynside® | Bacteria > *Bacteroidetes* | 4.9 | $3.60^{-10}$ |
| With Lynside® | Bacteria >> *Bacteroidia* | 4.9 | $3.60^{-10}$ |
| With Lynside® | Bacteria >>> *Bacteroidales* | 4.9 | $3.60^{-10}$ |
| With Lynside® | Bacteria >>>> *Bacteroidaceae* | 4.8 | $2.51^{-10}$ |
| With Lynside® | Bacteria >>>> *Bacteroides* | 4.8 | $2.51^{-10}$ |
| With Lynside® | Bacteria >>>>> *Bacteroides_uniformis* | 4.1 | $7.91^{-10}$ |
| With Lynside® | Bacteria >>>>> *Bacteroides_faecis* | 4.1 | $1.23^{-10}$ |
| With Lynside® | Bacteria >>>>>> *Bacteroides xylanisolyens* | 3.8 | $5.39^{-10}$ |
| With Lynside® | Bacteria >>>>> *Bacteroides ovatus* | 3.6 | $9.74^{-10}$ |
| Negative control | Bacteria >>>>>> *Bacteroides* Species | 3.9 | $4.02^{-10}$ |
| Negative control | Bacteria >>>>>> *Bacteroides vulgatus* | 3.6 | $4.35^{-10}$ |
| Negative control | Bacteria >>>>> *Bacteroides salyersiae* | 2.8 | $4.02^{-10}$ |
| Donor | Bacteria >>>>>> *Bacteroides cellulosilyticus* | 2.8 | $1.60^{-10}$ |
| Donor | Bacteria >>>>> *Bacteroides caccae* | 2.4 | $9.11^{-10}$ |

Note
The phylogenetic taxa are as follows Bacteria > *Bacteroidetes* > *Bacteroidia* > *Bacteroidales* > *Bacteroidaceae* > *Bacteroides* > *Bacteroides* species A significant and selective enrichment of substrate degraders present in the stool samples of all six studied donors in medium supplemented with the test substrate Lynside® Wall Basic was shown. Minor variations in metabolite composition were observed between donors, whereas no enterotype dependent pattern was observed. The results of next generation sequencing revealed a clear pattern with the enrichment of a clearly defined phylogenetic taxon, *Bacteroidetes*, in media supplemented with the test substrate Lynside® Wall Basic. Moreover, *Bacteroidetes* presented the best performance independently from the initial microbial composition of the donor, indicating the need for a complex set of enzymes for degradation of the substrate. These results demonstrate that Lynside® Wall Basic, which is a yeast cell wall product, stimulates the growth of bacteria of the *Bacteroidetes* phylum, such as bacteria of the *Bacteroides* genus, in the human gut microbiota.

Example 2

Prebiotic agent—Two materials were tested i.e. AGENT #1; and AGENT #2. Both materials are soluble sub-fractions free of yeast extract obtained after disruption treatment and then treatment with ribonucleases and glucanases, according to the method disclosed in the French application FR 3080521 A1 (1853748) filed on 27 Apr. 2018 and its related PCT application WO 2019/207111 A1. Both materials comprise 34.0 wt % total glucans (including 31.0 wt % β-glucans), and 31.0 wt % mannans, by mass on a dry matter basis. They have different particle sizes.

Nutritional medium—The nutritional medium is a sugar-depleted nutritional medium containing basal nutrients present in the colon (e.g. host-derived glycans such as mucin).

Dose—The prebiotic agents were tested at an optimal dose of 5 g/L, and against a blank (negative control).

Inoculum—As a source of the colonic microbiota, a freshly prepared human fecal inoculum was added.

Incubations—Incubations were performed for 48 h at 37° C., under shaking (90 rpm) and anaerobic conditions. This procedure allowed to assess the specific effect of test ingredients on the metabolic and community composition profile of the colonic microbiota.

Parameters measured—Different aspects were monitored, i.e. overall microbial fermentation (pH and gas production), changes in microbial activity to compare the kinetics in the production of bacterial metabolites (short-chain fatty acids or SCFAs, and lactate analysis), and changes in the microbial community composition (targeted qPCR and 16S-based illumina sequencing).

pH—The degree of acidification during the experiment is a measure for the intensity of bacterial metabolism of the potential prebiotic (fermentation). The pH of the incubations was determined at 0, 3, 6, 24 and 48 h after starting the incubation, thus giving a rough indication of the speed of fermentation of the different fiber blends.

Gas production—The colon incubations were performed in closed incubation systems. This allowed to evaluate the accumulation of gas in the headspace, which can be measured with a pressure meter. Gas production is a measure of microbial activity, and thus of the speed of fermentation of the potentially prebiotic substrates. $H_2$ and $CO_2$ are the first gasses to be produced upon microbial fermentation; they can subsequently be utilized as substrates for $CH_4$ production, reducing the gas volume. $H_2$ can also be utilized to reduce sulfate to $H_2S$, resulting from proteolytic fermentation. As a result, $N_2$, $O_2$, $CO_2$, $H_2$ and $CH_4$ constitute for 99% the volume of intestinal gas. The remaining 1% consists of $NH_3$, $H_2S$, volatile amino acids and short chain fatty acids. Gas production during the incubations was determined at 0, 3, 6, 24 and 48 h after starting the incubation.

SCFA analysis—The SCFA analysis is an assessment of the microbial carbohydrate metabolism (acetate, propionate and butyrate) and can be compared to typical fermentation patterns for normal GI microbiota. Samples for SCFA analysis were analyzed after 0, 3, 6, 24 and 48 h of incubation.

Lactate analysis—The human intestine harbors both lactate-producing and lactate-utilizing bacteria. Lactate is produced by lactic acid bacteria and decreases the pH of the environment, thereby also acting as an antimicrobial agent. Protonated lactic acid can penetrate the microbial cell after which it dissociates and releases protons within the cell, resulting in acidification and microbial cell death. It can also be rapidly converted into especially butyrate by other microorganisms. Samples for lactate analysis were analyzed after 0, 3, 6, 24 and 48 h of incubation.

Targeted qPCR—Quantitative PCR (qPCR) is a molecular technique that is based on the quantification of specific bacterial sequences (16S rRNA genes) through amplification. For the current project, a quantification of bifidobacteria and lactobacilli was performed at the start of the incubation, after 24 h and after 48 h.

16S-based Illumina sequencing—Because the Illumina sequencing method is PCR-based, microbial sequences are amplified till a saturation level is reached. Therefore, the results that are expressed at different phylogenetic levels (microbial phylum, family and genus or OTU level) are presented as proportional values versus the total amount of sequences within each sample, thus providing semi-quantitative results. The methodology applied involves primers that span 2 hypervariable regions (V3-V4) of the 16S rDNA. Using a pair-end sequencing approach, sequencing of 2×250 bp results in 424 bp amplicons. Such fragments are taxonomically more useful as compared to smaller fragments that are taxonomically less informative. Samples were taken at the beginning and at the end of the 48 h of incubation.

Results—The following results were obtained:

pH decrease—The pH was monitored. The pH measurements obtained are shown in table 3 below:

TABLE 3

| Time of incubation | AGENT #1 | AGENT #2 | Blank |
|---|---|---|---|
| 0 h | 6.59 | 6.53 | 6.55 |
| 3 h | 6.40 | 6.39 | 6.51 |
| 6 h | 6.25 | 6.26 | 6.49 |
| 24 h | 6.01 | 6.13 | 6.53 |
| 48 h | 5.98 | 6.05 | 6.44 |

The initial pH decrease (after 3 h and 6 h) was comparable between both products and stronger than the blank incubation.

The pH decrease of the products mainly occurred between 0-24 h, and was much stronger than for the blank. After 24 h fermentation, there was a slightly stronger pH decrease for AGENT #1 versus AGENT #2.

The pH remained relatively constant during the 24-48 h interval for the incubation with AGENT #1, while slightly further decreasing in the incubation with AGENT #2.

Stronger decreases in pH with prebiotic agents versus the blank consistently illustrated a high fermentability of both test products.

Gas production—The average gas production (kPa) in different time intervals upon fermentation of 5 g/L of the prebiotic agents tested and the negative control was monitored. The measurements obtained are shown in table 4 below:

TABLE 4

| Time interval | AGENT #1 | AGENT #2 | Blank |
|---|---|---|---|
| 24-48 h | 2.4 | 2.0 | 4.0 |
| 6-24 h | 26.2 | 22.9 | 10.9 |
| 3-6 h | 7.4 | 9.5 | 3.6 |
| 0-3 h | 9.1 | 10.5 | 5.5 |

The initial gas production (from 0-3 h and from 3-6 h) was considerably higher for AGENT #1 and for AGENT #2 than for the blank.

Gas production was highest within the 6-24 h period. In comparison to the blank both products suggested a high fermentation rate.

Both products resulted in a similar but small additional increase in gas production during the 24-48 h time interval, being slightly lower than the blank.

Higher levels of gas production with both prebiotic agents versus the blank consistently illustrated a high fermentability of both test products SCFA production—The average productions of acetate, propionate, butyrate and total SCFAs (mM) in different time intervals upon fermentation of 5 g/L of the prebiotic agents tested and the negative control were monitored.

The measurements obtained for the total SCFAs production (mM) are shown in table 5 below:

TABLE 5

| Time interval | AGENT #1 | AGENT #2 | Blank |
|---|---|---|---|
| 24-48 h | 4.5 | 7.2 | 6.5 |
| 6-24 h | 40.2 | 35.0 | 16.4 |
| 3-6 h | 8.6 | 10.6 | 3.6 |
| 0-3 h | 13.8 | 14.5 | 7.5 |

Both prebiotic agents strongly and similarly increased total SCFA levels to almost 70 mM, thus doubling the SCFA production compared to the control.

The measurements obtained for the lactate production (mM) are shown in table 6 below:

TABLE 6

| Time interval | AGENT #1 | AGENT #2 | Blank |
|---|---|---|---|
| 24-48 h | 0.2 | 1.7 | 1.0 |
| 6-24 h | 23.9 | 21.3 | 12.2 |
| 3-6 h | 4.7 | 6.0 | 2.1 |
| 0-3 h | 8.1 | 8.5 | 3.5 |

Both prebiotic agents doubled acetate levels compared to the negative control, with an increase of approximately almost 20 mM.

The measurements obtained for the propionate production (mM) are shown in table 7 below:

TABLE 7

| Time interval | AGENT #1 | AGENT #2 | Blank |
|---|---|---|---|
| 24-48 h | 1.5 | 2.6 | 2.3 |
| 6-24 h | 15.8 | 13.0 | 3.6 |
| 3-6 h | 3.9 | 4.5 | 1.4 |
| 0-3 h | 3.4 | 3.7 | 1.8 |

Like acetate, propionate can be produced by a wide range of gut microbes, with the most abundant propionate producers being *Bacteroides* spp. (phylum=*Bacteroidetes*) and *Akkermansia muciniphila* (phylum=Verrucomicrobia). As the latter is a mucin-degrading microbe, the observed propionate productions can probably be attributed to *Bacteroides* spp. Again, both products more than doubled the final propionate levels versus the negative control.

The measurements obtained for the butyrate production (mM) are shown in table 8 below:

TABLE 8

| Time interval | AGENT #1 | AGENT #2 | Blank |
|---|---|---|---|
| 24-48 h | 1.08 | 1.30 | 1.03 |
| 6-24 h | 4.20 | 4.11 | 2.54 |
| 3-6 h | 0.25 | 0.30 | 0.12 |
| 0-3 h | 0.46 | 0.50 | 0.17 |

Butyrate production was strongly increased upon administration of both products.

In conclusion, both prebiotic agents doubled total SCFA production compared to the control. This increase was related to the increased production of acetate, propionate and butyrate that were all three almost doubled versus the control. In agreement with the results of the pH and gas production, the increases were strongest during the first 24 h, indicating a high fermentation rate induced by both products.

Lactate production—The average lactate production (mM) in different time intervals upon fermentation of 5 g/L of the prebiotic agents tested and the negative control was monitored.

The measurements obtained for the lactate production (mg/L) are shown in table 9 below:

TABLE 9

| Time interval | AGENT #1 | AGENT #2 | Blank |
|---|---|---|---|
| 24-48 h | −0.43 | −0.24 | −0.12 |
| 6-24 h | −1.28 | −1.61 | 0.01 |
| 3-6 h | −0.17 | −0.19 | −0.21 |
| 0-3 h | 1.90 | 2.16 | 0.71 |

Both prebiotic agents resulted in high initial lactate production (0-3 h) compared to the control. From 3 h of incubation onwards lactate was consumed, with mild consumption during the 3-6 h and 24-48 h periods and highest consumption during the 6-24 h timeframe. Lactate consumption within the 6-24 h timeframe corresponds well to high butyrate production that mainly occurred in this time frame, thus indicating that lactate might have served as precursor of butyrate.

Bifidobacteria level—The level of bifidobacterial (average absolute *Bifidobacterium* numbers expressed as 16S rRNA gene copies/mL) at different time points upon fermentation of 5 g/L of the prebiotic agents tested and the negative control was monitored.

The average absolute *Bifidobacterium* numbers, expressed as 16S rRNA gene copies/mL, are shown in table 10 below:

TABLE 10

| Time of incubation | AGENT #1 | AGENT #2 | Blank |
|---|---|---|---|
| 0 h | BDL | BDL | BDL |
| 24 h | $1.9 \times 10^5$ | $2.0 \times 10^5$ | $1.8 \times 10^5$ |
| 48 h | $1.8 \times 10^5$ | $2.1 \times 10^5$ | $2.0 \times 10^5$ |

BDL: below detection limit

At the start of the incubation, *Bifidobacterium* levels were below the limit of detection. During the incubation, Bifidobacteria were enriched in a similar way as the blank. As such, no stimulatory effect of the treatments on Bifidobacteria was observed.

Lactobacilli level—The level of *Lactobacillus* (average absolute *Lactobacillus* numbers expressed as 16S rRNA gene copies/mL) at different time points upon fermentation of 5 g/L of the prebiotic agents tested and the negative control was monitored.

The average absolute *Lactobacillus* numbers, expressed as 16S rRNA aerie copies/mL, are shown in the table 11 below:

TABLE 11

| Time of incubation | AGENT #1 | AGENT #2 | Blank |
|---|---|---|---|
| 0 h | $1.5 \times 10^5$ | $1.5 \times 10^5$ | $1.5 \times 10^5$ |
| 24 h | $1.2 \times 10^6$ | $2.5 \times 10^6$ | $2.7 \times 10^6$ |
| 48 h | $1.7 \times 10^6$ | $2.7 \times 10^6$ | $2.5 \times 10^6$ |

The prebiotic agents did not stimulate *Lactobacillus* levels versus the blank.

16S-targeted Illumina sequencing (phylum level)—The relative abundance (%) of the different phyla in the original inoculum and in the colon incubations upon addition of the prebiotic agents versus the blank was determined.

The relative abundance of the different phyla is shown in table 12 below:

TABLE 12

| Phylum | Inoculum | AGENT #1 | AGENT #2 | Blank |
|---|---|---|---|---|
| Actinobacteria | 3.8% | 0.6% | 0.6% | 1.3% |
| Bacteroidetes | 45.2% | 78.5% | 69.7% | 58.2% |
| Firmicutes | 50.9% | 13.1% | 19.3% | 20.5% |
| Proteobacteria | 0.1% | 7.9% | 10.4% | 20.1% |

All major phyla that were originally present in the inoculum were also preserved during the in vitro incubations. Both prebiotic agents enriched the *Bacteroidetes* levels after 48 h of incubation, when compared to both the original inoculum as well as when compared to the blank. The proportion of *Bacteroidetes*, containing many propionate-producing species, was higher in the incubations with AGENT #1 (78.5%) versus AGENT #2 (69.7%), which was in line with the slightly higher propionate concentrations that were associated with fermentation for this product. Due to the strong increase of *Bacteroidetes*, the relative abundance of *Firmicutes* significantly decreased during incubations with the test products.

16S-targeted Illumina sequencing (family and OTU)—The relative abundance (%) of bacteria of *Bacteroidetes* phylum/Bacteroidaceae family and *Firmicutes* phylum/Erysipelotrichaceae family in the original inoculum and in the colon incubations upon addition of the prebiotic agents versus the blank was determined.

The relative abundance of bacteria of *Bacteroidetes* phylum/Bacteroidaceae family and bacteria of *Firmicutes* phylum/Erysipelotrichaceae family is shown in table 13 below:

TABLE 13

| Phylum Family | Inoculum | AGENT #1 | AGENT #2 | Blank |
|---|---|---|---|---|
| Bacteroidetes Bacteroidaceae | 43.1% | 78.0% | 69.1% | 57.2% |
| Firmicutes Erysipelotrichaceae | 1.0% | 4.1% | 8.4% | 0.1% |

In the inoculum, the remaining proportion of bacteria of the *Bacteroidetes* phylum comprised essentially of bacteria of Porphyromonadaceae family (1.3%) and of bacteria of Rikenellaceae family (0.8%).

It is shown a stronger enrichment of Bacteroidaceae and Erysipelotrichaceae by the prebiotic agents, than in the blank.

Amongst the bacteria of *Bacteroidetes* phylum/Bacteroidaceae family, the relative abundance of the species *Bacteroides ovatus* was determined. Likewise, amongst the bacteria of *Firmicutes* phylum/Erysipelotrichaceae family, the relative abundance of the species *Clostridium* XVIII (OTU5) was determined. The data is shown in table 14 below:

TABLE 14

| Species | AGENT #1 | AGENT #2 | Blank |
|---|---|---|---|
| *Bacteroides ovatus* | 68.4% | 57.0% | 9.8% |
| Erysipelotrichaceae *Clostridium* XVIII OTU5 | 3.9% | 8.1% | 0.0% |

Amongst the bacteria of the Bacteroidaceae family, the prebiotic agents induced a very strong enrichment in *Bacteroides ovatus* versus the blank. Amongst the bacteria of the Erysipelotrichaceae family, the prebiotic agents induced a very strong enrichment of *Clostridium* XVIII versus the blank.

Conclusion—The potential of the prebiotic agents tested was assessed in short-term colonic incubations and was compared to a negative control i.e. incubation without fibers. Multiple endpoints demonstrated the large prebiotic potential of both agents, resulting in: (1) a pH decrease and increase in gas production; (2) an increase in production of the health-promoting SCFA acetate, propionate and butyrate; (3) the stimulation of the initial lactate production, followed by consumption, probably leading to increased butyrate concentrations. Further, no stimulatory effect of both prebiotic agents towards Bifidobacteria and Lactobacilli could be observed. In addition, a stimulatory effect of prebiotic agents on *Bacteroidetes*, particularly on *Bacteroides ovatus*, could be observed, thus explaining their stimulatory effect on acetate and propionate production.

What is claimed is:

1. A method for stimulating growth of a bacterium of the *Bacteroidetes* phylum in a gut of a mammal, the method comprising:
    selecting a mammal in need of stimulated growth of bacteria of the *Bacteroidetes* phylum in the gut of the mammal;
    preparing a yeast product by subjecting a yeast cream to plasmolysis at a temperature between 70° C. and 95° C., treating at 60° C. with a mix of two glucanases and a mix of endo and exo-ribonucleases, centrifuging to obtain an insoluble yeast protein extract, and washing the insoluble yeast protein extract to obtain the yeast product;
    administering the yeast product as a prebiotic agent to the mammal; and
    stimulating growth of the bacterium of the *Bacteroidetes* phylum in the gut of the mammal,
    wherein the yeast product comprises walls of yeast cells or a fraction thereof.

2. The method according to claim 1, wherein the yeast is selected from the group consisting of the genera *Saccharomyces, Pichia, Candida, Kluyveromyces, Yarrowia* and/or *Wickehomomyces*.

3. The method according to claim 1, wherein the bacterium of the *Bacteroidetes* phylum is bacterium of the *Bacteroidia* class.

4. The method according to claim 1, wherein the yeast product increases the ratio of the bacterium of the *Bacteroidia* phylum versus a bacterium of the *Firmicutes* phylum in the gut microbiota.

5. The method according to claim 1, wherein the prebiotic agent is selected from the group consisting of deactivated whole yeasts, yeast cell walls, fractions of the yeast cell walls, and mixtures thereof.

6. The method according to claim 1, wherein the yeast product is a fraction obtained using a disruption treatment.

7. The method according to claim 1, wherein the yeast product is a soluble sub-fraction obtained by submitting whole yeast cells to a disruption treatment, separating a soluble fraction from an insoluble fraction, then treating the insoluble fraction with ribonucleases and glucanases, before separating a protein-rich insoluble sub-fraction from a soluble sub-fraction.

8. The method according to claim 1, wherein the yeast product is a soluble fraction obtained by submitting whole yeast cells to a disruption treatment, then treating the mixture obtained with ribonucleases and glucanases, before separating a protein-rich insoluble sub-fraction from a soluble sub-fraction.

9. The method according to claim 1, wherein the yeast product has a β-glucan content (expressed as equivalent mass of glucose) from 15 to 50% by mass on a dry matter basis; and/or a mannan content (expressed as equivalent mass of mannose) from 10 to 40% by mass on a dry matter basis.

10. The method according to claim 1, wherein the yeast product comprises a dry matter content of at least 90%, from 15 to 50% of a β-glucan content (expressed as equivalent mass of glucose), from 10 to 40% of a mannan content (expressed as equivalent mass of mannose), from 5 to 15% of additional proteins, from 5 to 15% of free nucleotides, from 2 to 8% of free amino acids and peptides of 1 kDaltons or less, 2% or less of oligosaccharides, from 6 to 11% of ashes and from 1 to 3% of fat components and a dry matter content of at least 90%.

11. The method according to claim 1, wherein the yeast product does not stimulate the growth of a bacterium of the *Bifidobacterium* genus and/or a bacterium of the *Lactobacillus* genus.

12. The method according to claim 1, wherein the yeast product is administered orally.

13. The method according to claim 1, wherein the yeast product is administered in a composition formulated as a gum, a tablet, a capsule, a pill, a powder, granules or a suspension.

14. The method of claim 1, wherein the mammal in need of stimulated growth of bacteria of the *Bacteroidetes* phylum in the gut of the mammal benefits from stimulated immunity, regulated glycemia and/or lipidemia, or limited metabolic disorders associated with obesity.

15. The method of claim 1, wherein the yeast is selected from the group consisting of the species *Saccharomyces cerevisiae, Pichia jadinii*, and *Kluyveromyces marxianus*.

16. The method according to claim 3, wherein the bacterium is a bacterium of the *Bacteroides* genus.

17. The method according to claim 16, wherein the bacterium is *Bacteroides ovatus* spp.

18. The method according to claim 6, the yeast product is the insoluble portion of yeast cells obtained using the disruption treatment.

19. The method according to claim 12, wherein the yeast product is administered orally at a daily dose from 500 mg to 15 g in up to 10 takings.

20. The method according to claim 14, wherein the metabolic disorder associated with obesity is diarrhea or irritable bowel syndrome.

21. The method of claim 1, wherein the yeast product comprises 34 wt % total glucans and 31 wt % mannans.

22. A method for improving a gut microbiota, the method comprising:
- identifying a subject in need of an improved gut microbiota;
- administering to the subject the yeast product of claim 1; and
- stimulating growth of a bacterium of the *Bacteroidetes* phylum in a gut of the subject;
- thereby improving the gut microbiota in the subject and preventing or limiting one or more gut pathologies in the subject.

23. The method of claim 1, wherein the mammal in need of stimulated growth of bacteria of the *Bacteroidetes* phylum in the gut of the mammal is not selected on the bases of having a need for regulation of glycemia or immune stimulation.

* * * * *